United States Patent
Baid

(10) Patent No.: US 8,337,471 B2
(45) Date of Patent: Dec. 25, 2012

(54) NEEDLE SAFETY DEVICE

(75) Inventor: Rishi Baid, New Delhi (IN)

(73) Assignee: Poly Medicure Ltd., New Delhi (IN)

( * ) Notice: Subject to any disclaimer, the term of this patent is extended or adjusted under 35 U.S.C. 154(b) by 245 days.

(21) Appl. No.: 12/669,032

(22) PCT Filed: Jul. 10, 2008

(86) PCT No.: PCT/IB2008/001823
§ 371 (c)(1),
(2), (4) Date: Apr. 29, 2010

(87) PCT Pub. No.: WO2009/010847
PCT Pub. Date: Jan. 22, 2009

(65) Prior Publication Data
US 2010/0222749 A1    Sep. 2, 2010

(30) Foreign Application Priority Data

Jul. 17, 2007    (EP) .................................... 07013976

(51) Int. Cl.
*A61M 25/00* (2006.01)

(52) U.S. Cl. ..................................... 604/263

(58) Field of Classification Search ............ 604/165.01, 604/236, 263
See application file for complete search history.

(56) References Cited

U.S. PATENT DOCUMENTS

| | | | |
|---|---|---|---|
| 4,863,434 A * | 9/1989 | Bayless | 604/198 |
| 5,215,525 A | 6/1993 | Sturman | |
| 5,344,408 A * | 9/1994 | Partika | 604/192 |
| 6,203,527 B1 * | 3/2001 | Zadini et al. | 604/110 |
| 6,616,630 B1 * | 9/2003 | Woehr et al. | 604/110 |
| 7,112,191 B2 * | 9/2006 | Daga | 604/263 |
| 7,976,502 B2 * | 7/2011 | Baid | 604/164.01 |
| 2005/0277879 A1 * | 12/2005 | Daga | 604/110 |
| 2006/0155245 A1 | 7/2006 | Woehr | |
| 2007/0191776 A1 | 8/2007 | Bialecki et al. | |
| 2009/0299291 A1 * | 12/2009 | Baid | 604/164.08 |
| 2010/0222749 A1 * | 9/2010 | Baid | 604/263 |
| 2011/0060294 A1 * | 3/2011 | Baid | 604/263 |
| 2011/0125096 A1 * | 5/2011 | Baid | 604/164.08 |

FOREIGN PATENT DOCUMENTS

| | | |
|---|---|---|
| CA | 2133053 A1 | 3/1995 |
| DE | 44 34 569 A1 | 3/1995 |
| DE | 203 15 872 U1 | 10/2003 |

(Continued)

*Primary Examiner* — Nicholas Lucchesi
*Assistant Examiner* — Diva K Chander
(74) *Attorney, Agent, or Firm* — Kilpatrick Townsend and Stockton LLP

(57) ABSTRACT

The invention relates to a needle safety device for a medical device. The needle safety device includes: a base portion having a bore extending therethrough for receiving a needle; and two opposing jaws extending from the base portion each having a head portion in the region of its free end. At least one of the head portions forms a locking shoulder for securing the needle safety device in a housing of the medical device. An elastic element surrounds the jaws in a region between the base portion and the head portions. The jaws can be spread apart against a restoring force of the elastic element in order to allow the needle received in the bore to extend all the way-through the needle safety device. The invention also relates to a needle for a medical device and to an intravenous catheter apparatus comprising a needle and a needle safety device.

27 Claims, 6 Drawing Sheets

FOREIGN PATENT DOCUMENTS

| | | |
|---|---|---|
| DE | 20 2007 009 977 U1 | 11/2007 |
| EP | 0 750 918 A2 | 1/1997 |
| EP | 1 180 381 A1 | 4/2001 |
| GB | 2 292 525 A | 2/1996 |
| WO | WO 97/31666 A1 | 9/1997 |
| WO | WO 03/011381 A1 | 2/2003 |
| WO | WO 2004/004819 A | 1/2004 |
| WO | WO 2005/079891 A1 | 9/2005 |

* cited by examiner

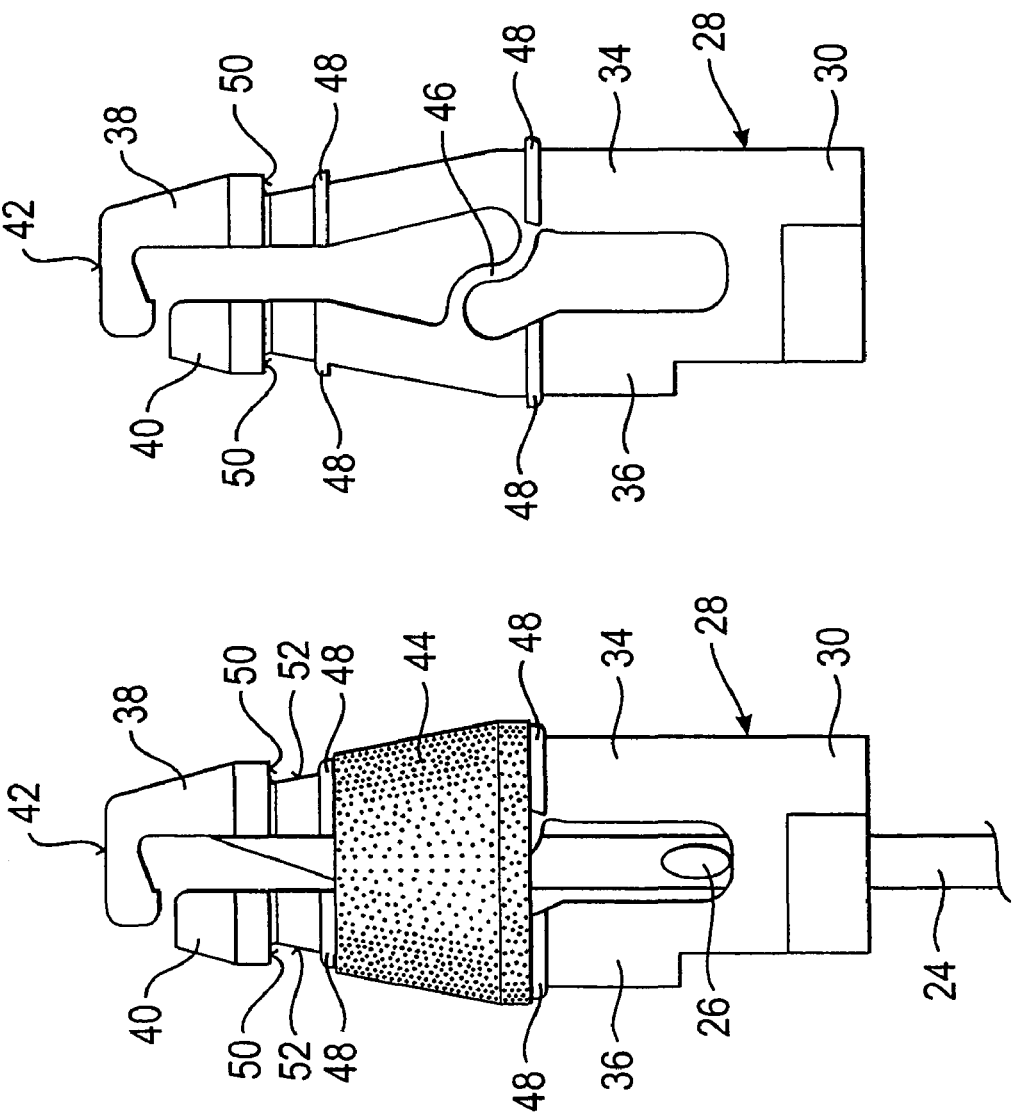

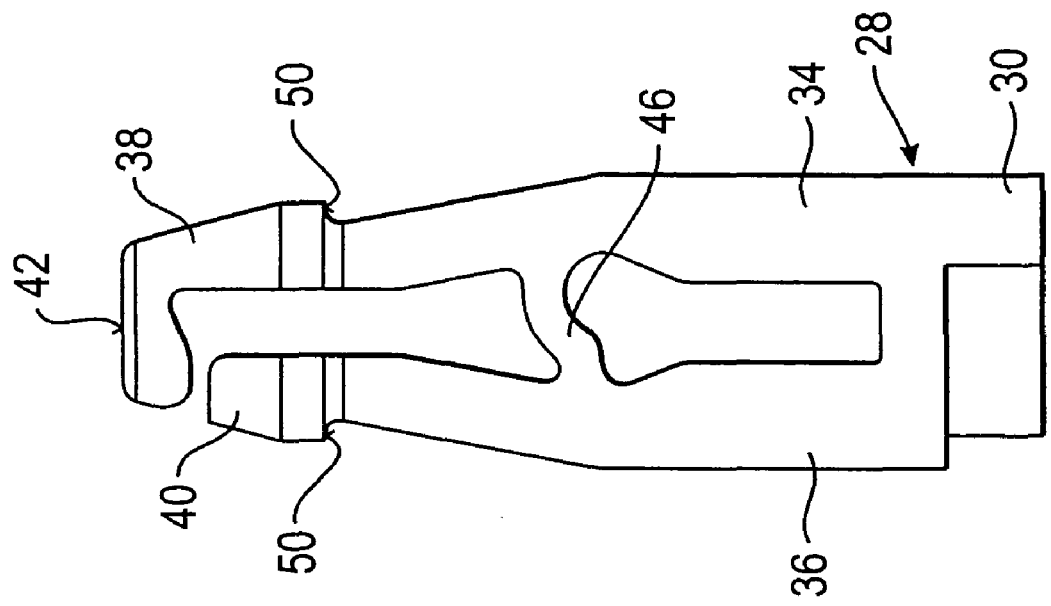
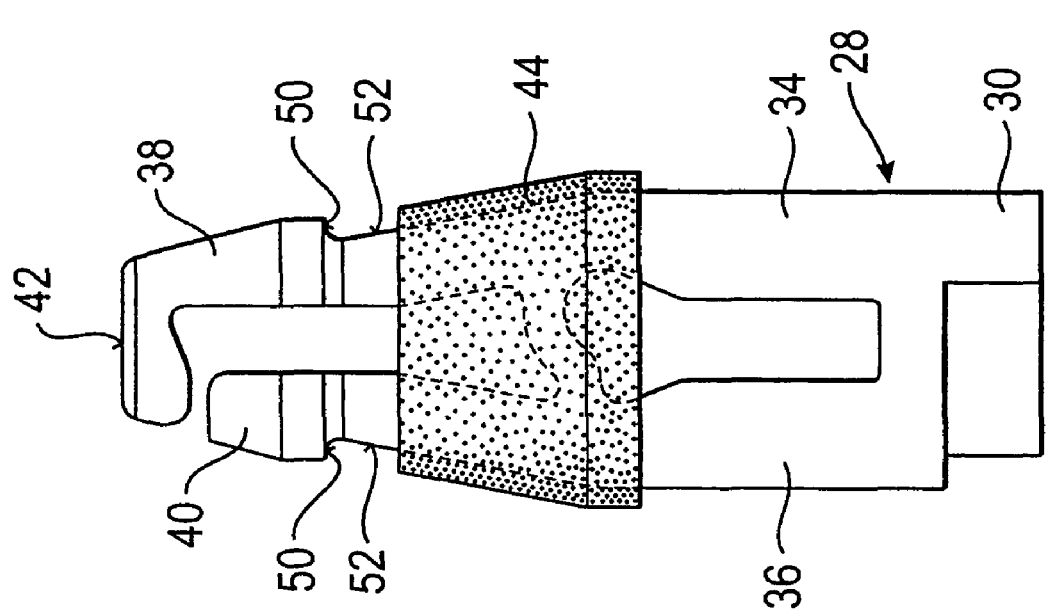

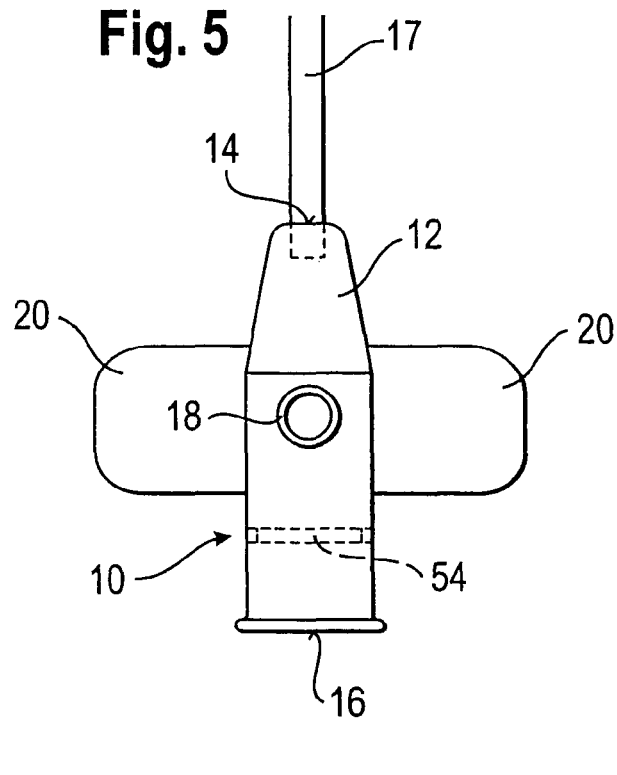
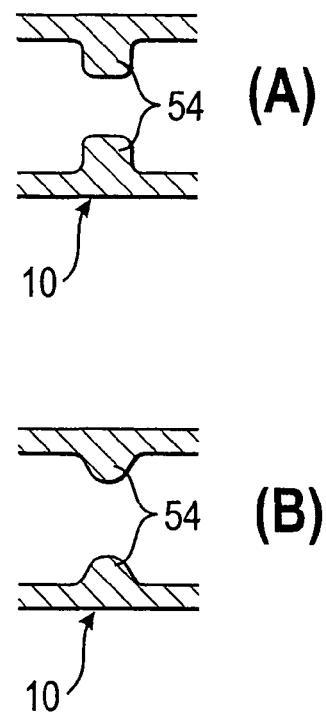
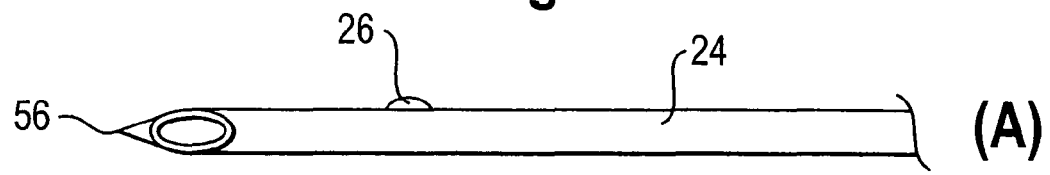
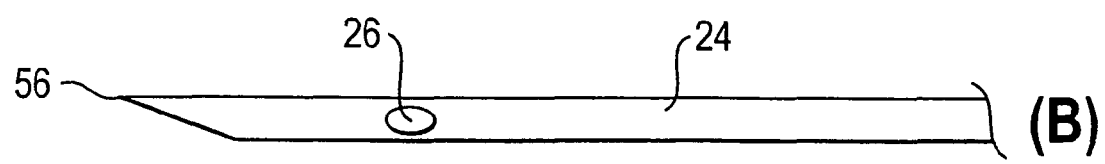

NEEDLE SAFETY DEVICE

CROSS-REFERENCES TO RELATED APPLICATIONS

This application is a National Stage of International Application No. PCT/IB2008/001823 filed Jul. 10, 2008, and which claims the benefit of European Patent Application No. 07013976.1, filed Jul. 17, 2007, the disclosures of which are incorporated herein by reference.

The present invention relates to a needle safety device for a medical device such as, for example, an intravenous catheter apparatus, which comprises a base portion having a bore extending in an axial direction therethrough for receiving a needle, and two opposing jaws extending from the base portion generally in the axial direction and each having a head portion in the region of its free end, wherein at least one of the head portions forms a locking shoulder for securing the needle safety device in a housing of the medical device.

A needle safety device of this kind is generally known and operative as a guard for the tip of a needle of the medical device by automatically covering the needle tip during withdrawal of the needle from a patient. The needle safety device thereby serves to prevent accidental pricking of, for example, a medical professional by the needle after removal of the needle from the medical device.

It is an object of the invention to provide a needle safety device which provides a better protection against accidental pricking by the needle.

This object is satisfied by a needle safety device having the features of claim 1.

The needle safety device of the invention is characterized by an elastic element at least partly surrounding the jaws in a region between the base portion and the head portions, wherein the elastic element and the jaws are configured such that the jaws can be spread apart against a restoring force of the elastic element in order to allow the needle received in the bore to extend all the way through the needle safety device.

Due to the elastic element exerting its restoring force on the jaws in the spread apart state of the jaws, which is the state in which the medical device, for example, an intravenous catheter apparatus, is typically shelved prior to use, the elastic element ensures that the spread apart jaws will snap together and guard the needle tip upon withdrawal of the needle from the medical device even after a longer shelf time, thereby continuously ensuring a correct functioning of the needle safety device. In addition, the elastic element prevents the jaws from becoming loose when the needle safety device slides along the needle, thereby further aiding a correct functioning of the needle safety device.

As a result of the elastic element being arranged in a region between the base portion and the head portions of the jaws, the elastic element also helps prevent the needle tip from protruding sideways out of the needle safety device, thereby further increasing the protecting function of the needle safety device.

Furthermore, due to the arrangement of the elastic element between the base portion and the head portions of the jaws, a locking recess for receiving a locking protrusion formed inside the housing of the medical device is formed between the elastic element and the locking shoulder of the at least one head portion. When the locking protrusion engages with the recess formed by the shoulder of the at least one head portion and the elastic element, the needle safety device is safely secured inside the housing of the medical device and is, in particular, prevented from movement in the axial direction relative to the housing.

The elastic element may comprise a tension ring completely surrounding the jaws, and/or a clamp, bracket, "C" clip or the like surrounding the jaws only in part.

According to a preferred embodiment, as seen in the axial direction, the elastic element covers a substantial part of the jaws. The elastic element forms a partial sidewall and together with the jaws defines a chamber inside the needle safety device, in which the needle tip is held after complete withdrawal of the needle from the medical device, thereby further increasing the guarding function of the needle safety device.

The axial dimension of the elastic element may range from about one fifth of the length of the jaws to about two thirds or three fourths of the length of the jaws, and preferably is in the range of about one third of the length of the jaws.

Preferably, the elastic element is made from a material having elastic properties, for example, an elastic material such as rubber, silicone or the like. Due to its elastic properties, the elastic element creates a restoring force on the jaws, when the needle fully extends through the needle safety device thereby spreading the jaws apart and expanding the elastic element. As soon as the needle tip passes the free ends of the jaws upon pulling the needle through the needle safety device, the jaws are positively collapsed by the elastic element due to its restoring force.

In accordance with a further embodiment, the jaws are connected to each other by at least one link in a region between the base portion and the head portions. Preferably, the link is arranged in the region of the elastic element. The link may be provided on only one side of the jaws. Alternatively, first and second links may be provided on opposite sides of the jaws.

Preferably, the at least one link is formed to have spring-like properties such that the jaws can be spread apart against a restoring force of the link. For example, the link may have a curved shape, such as an S- or Z-like shape. Alternatively, the link may have a substantially straight shape.

The at least one link prevents the two jaws from spreading apart two far, thus preventing over-stretching of the elastic element which could result in a loss of elastic properties. Furthermore, the link supports the elastic element in exerting a force on the jaws in the collapsing direction, thereby aiding the elastic element in preventing the jaws from becoming loose when the needle safety device slides along the needle. In addition, the link causes the jaws to collapse even if the elastic element should fail in its function. The link is designed such that it retains its spring-like properties over the period of shelf live.

To allow for a simplified and cost-effective production of the needle safety device, the base portion, the jaws, and preferably also the at least one link may be integrally formed and preferably made from a plastic material, for example, by injection molding. Alternatively, the base portion, the jaws, and preferably also the at least one link may be made from a metal material. According to a further embodiment, the base portion, the jaws and/or the link each comprise a different material or combination of materials, such as a different plastic material, a different metal material or a different combination of plastic and/or metal materials. For example, the base may be made from a metal material and the jaws may be made from a plastic material, or vice versa. It is also considered that the inner part of the jaws, which contacts the needle, is made from a thermoplastic material such as TPE, whereas the outer part of the jaws may be made from a different material, for example, a plastic, metal, composite or elastomer material, so that the needle safety device causes less friction when sliding along the needle thereby facilitating the withdrawal of the needle.

In order to prevent the needle tip guarded by the needle safety device from protruding beyond the free ends of the jaws, at least one of the jaws has an angled end section at its free end, which extends towards the other one of the jaws in a direction generally perpendicular to the axial direction.

Preferably, the length of the at least one angled end section is selected such that the angled end section is supported on the needle when the needle extends all the way through the needle safety device, thereby spreading the jaws apart far enough for the shoulder of the head portion of the jaw having the angled end section to be able to engage behind the locking protrusion provided in the housing of the medical device.

Further subject matter of the invention is a needle for a medical device such as, for example, an intravenous catheter apparatus, which has an inner profile, i.e. cross-section area defined by the inner periphery or circumference of the needle, a principal outer profile, i.e. principal cross-section area defined by the outer periphery or circumference of the needle, and a needle tip, the needle further comprising at least one enlargement in the region of the needle tip, wherein the enlargement is formed from an increase of the outer profile, whereas the inner profile remains substantially unchanged.

Still further subject matter of the invention is a medical device, in particular an intravenous catheter apparatus, comprising a needle of the aforementioned type and a needle safety device, in particular of the above described kind, which is slidably arranged on the needle for protecting the needle tip, wherein the needle safety device includes a base portion having a bore extending therethrough for receiving the needle, the bore being adapted to the principal outer profile of the needle.

The enlargement and thus increase in effective diameter in the region of the needle tip prevents the needle tip from being pulled through the base portion of the needle safety device during withdrawal of the needle from the medical device. In other words the enlargement prevents the needle safety device from sliding beyond the needle tip and thus ensures that the needle tip is continuously and reliably guarded by the needle safety device after removal of the needle from the medical device.

By forming the enlargement such that only the outer profile of the needle is increased, whereas the inner profile remains unchanged, in other words by maintaining a substantially constant inner cross-section area throughout the entire length of the needle, blood from a patient entering the needle can freely flow along the inside of the needle. In other words a flashback of blood, which occurs when the needle penetrates a vein, is not adversely affected by the enlargement.

The enlargement may be formed by subjecting the needle to concentrated heat at a localized area using, for example, a welding process such as a laser welding process, with or without addition of additional material.

Alternatively, the enlargement may be formed from additional material dispensed onto the outer surface of the needle. In order to locate the dispensed material in a defined position, a recess or groove may be formed in the outer surface or circumference of the needle.

The additional material may, for example, be selected from at least one of a plastic material, an adhesive, a resin and a metal material.

In the case of the additional material being a metal material, the enlargement may, for example, be formed by build-up welding of the additional material onto the needle.

Preferred embodiments of the invention are described in the following description and in the accompanying drawings, wherein:

FIG. 3A shows a side view of the needle safety device of FIG. 1 including a tension ring, with the needle safety device guarding the tip of the needle;

FIG. 3B shows a side view of the needle safety device of FIG. 3A without the needle or the tension ring;

FIG. 3C shows a depression for receiving a tension ring, which is formed in the outer surface of a needle safety device according to an alternative embodiment of the invention;

FIG. 4A shows a side view of an alternative embodiment of the needle safety device of the invention, including a tension ring;

FIG. 4B shows a side view of the needle safety device of FIG. 4A without the tension ring;

FIG. 5 shows a plan view of the wing housing of FIG. 1;

FIG. 6A shows a cross-sectional view of a section of the wing housing of FIG. 5 detailing an annular locking protrusion;

FIG. 6B shows a cross-sectional view of a section of the wing housing of FIG. 5 detailing an alternative embodiment of the annular locking protrusion;

FIG. 7A shows a side view of the needle tip region of the needle of FIG. 1 showing the details of an enlargement formed on the outer surface of the needle;

FIG. 7B shows a plan view of the needle tip region of FIG. 7A;

Figure 1:
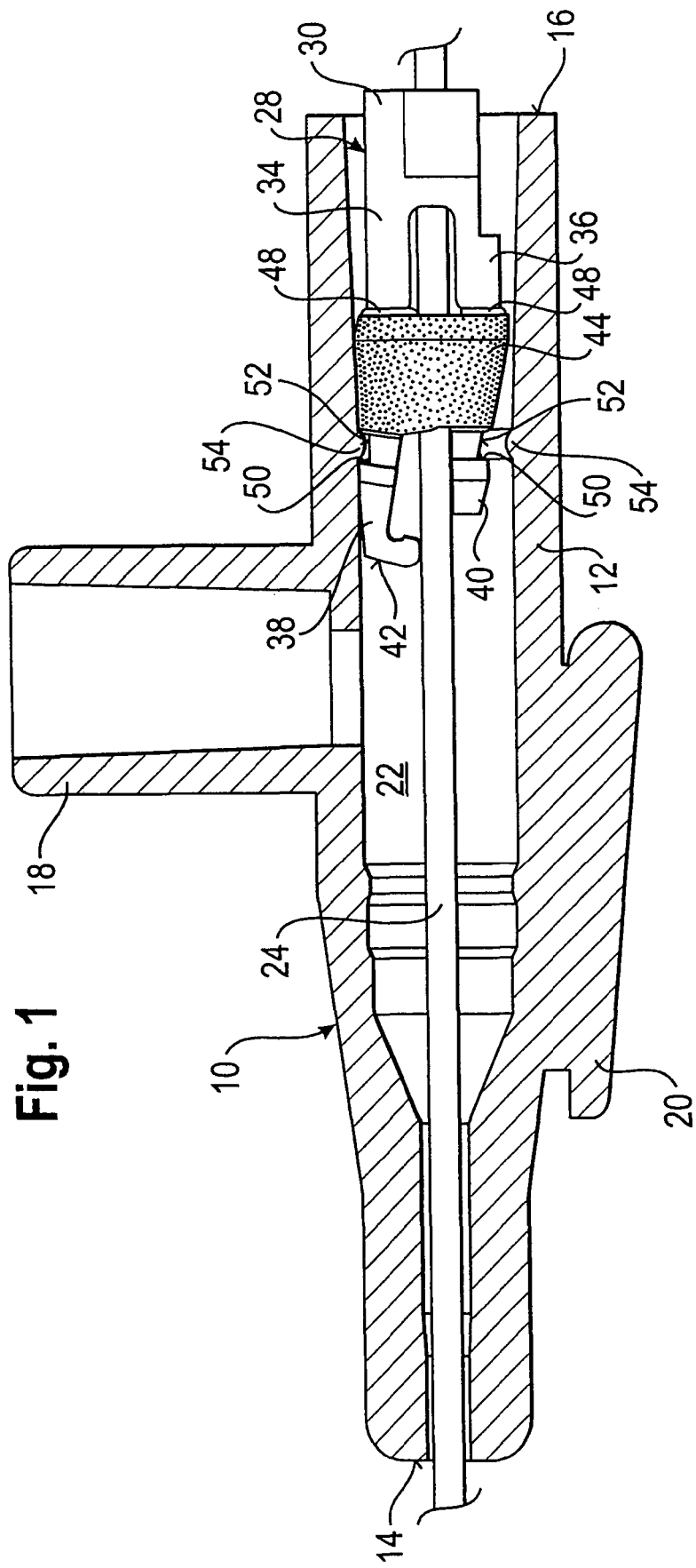
FIG. 1 shows a view partly in cross-section of a wing housing of an intravenous catheter apparatus, including a needle safety device of the invention inserted therein and a needle extending therethrough.

Referring to FIG. 1, a catheter hub or wing housing 10 of an intravenous catheter apparatus is shown. The wing housing 10 comprises a main body 12 of generally tubular form and extending in an axial direction. The main body has a distal end 14 and a proximal end 16. A catheter 17 (FIG. 5) is attached to the main body 12 at the distal end 14 of the main body 12. A port 18 extends from the main body 12 in a direction generally perpendicular to the axial direction. Wings 20 (FIG. 5) are provided at the main body 12 opposite from the port 18. The main body 12 defines a chamber 22 extending from the proximal end 16 towards the distal end 14.

Prior to use of the intravenous catheter apparatus, a needle 24 extends through the wing housing 10 in the axial direction. The needle 24 has an inner profile, i.e. cross-section area defined by the inner periphery or circumference of the needle 24, which is substantially constant across the length of the needle 24. A principal outer profile, i.e. principal cross-section area defined by the outer periphery or circumference of the needle 24, is also substantially constant across the length of the needle 24 except for an enlargement 26 of the needle 24 provided in the region of the needle tip at the distal end of the needle 24, which will be described in more detail below with reference to FIGS. 7 to 9.

Still referring to FIG. 1, a needle safety device 28 is slideably arranged on the needle 24. Prior to use of the intravenous catheter apparatus, the needle safety device 28 is inserted into the chamber 22 from the proximal end 16 of the main body 12.

As can be seen from FIGS. 1, 3 and 4, the needle safety device 28 comprises a base portion 30 which has a bore extending in the axial direction therethrough for receiving the needle 24. The bore is matched in shape and size to the principal outer profile of the needle 24.

First and second jaws 34, 36 extend from the base portion 30 generally in the axial direction. The first jaw 34 has a first head portion 38 in the region of its free end, and the second jaw 36 has a second head portion 40 in the region of its free end. The first head portion 38 extends beyond the second head portion 40 and has an angled end section 42 at its free end, which extends towards the second jaw 36 in a direction generally perpendicular to the axial direction.

Figure 2:
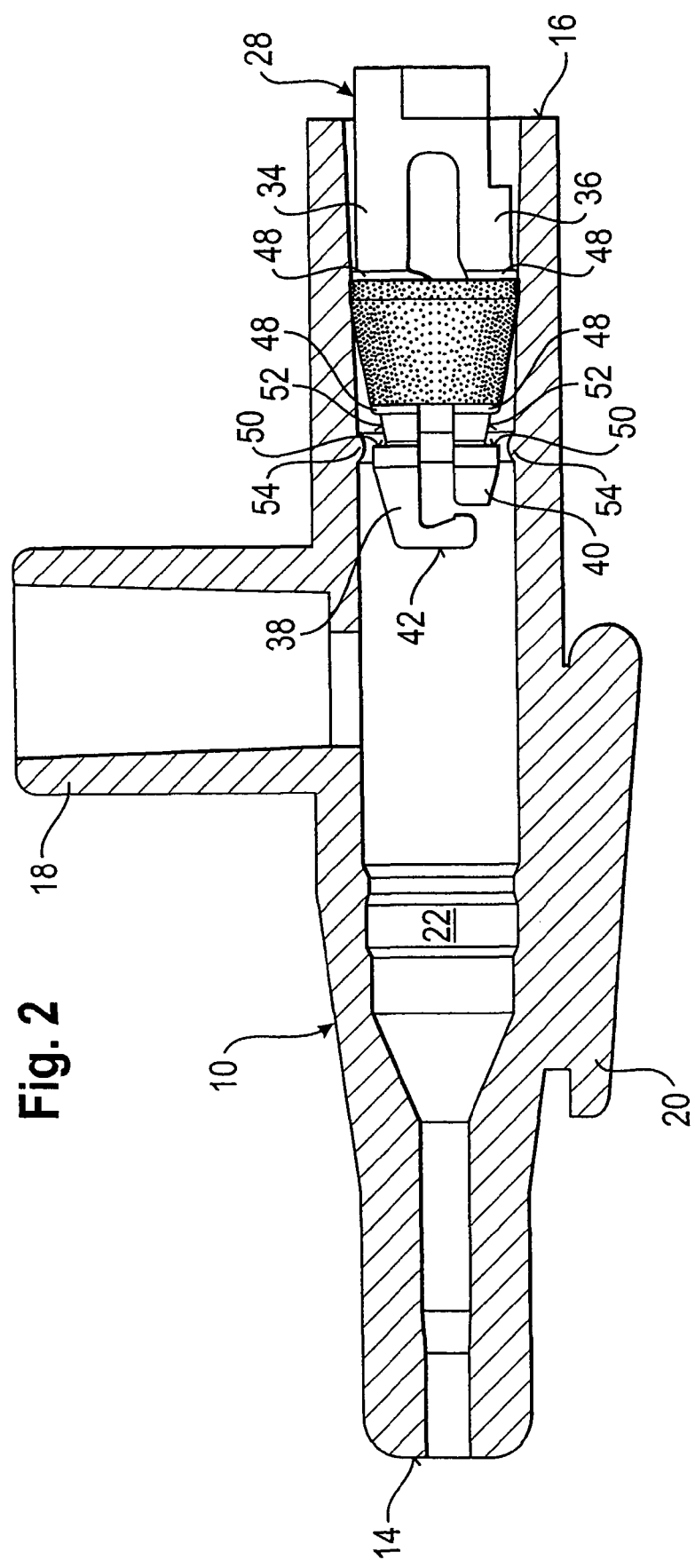
FIG. 2 shows a view partly in cross-section of the wing housing of FIG. 1, including the needle safety device, but not the needle.

The length of the angled end section 42 is selected such that the angled end section 42 protrudes over at least a part of the second head portion 40, when the jaws 34, 36 are in a relaxed position as is shown in FIGS. 2, 3 and 4. When the needle 24 extends all the way through the needle safety device 28, such as prior to use of the intravenous catheter device as shown in FIG. 1, the angled end section 42 is supported on the needle 24, whereby the first jaw 34 is forced away from the second jaw 36 from its relaxed position into a spread apart position.

The jaws 34, 36 are surrounded by a tension ring 44 in a region between the base portion 30 and the head portions 38, 40. The tension ring 44 is made from an elastic material, such as rubber, silicone or the like. The tension ring 44 is fitted around the jaws 34, 36 such that it exerts a restoring force on the jaws 34, 36, when the jaws are spread apart by the needle 24, as shown in FIG. 1.

As is illustrated in FIGS. 1, 2, 3A and 4A, the tension ring 44 covers a substantial part of the jaws 34, 36 seen in the axial direction. Specifically, the axial dimension of the tension ring may range from about one fifth of the length of the jaws to about two thirds or three fourth of the length of the jaws, and preferably is in the range of about one third of the length of the jaws.

Referring to FIGS. 3B and 4B, the jaws 34, 36 are connected to each other by a link 46. The link 46 is arranged approximately half way along the length of the jaws 34, 36 between the base portion 30 and the head portions 38, 40, i.e. in the region of the tension ring 44. More specifically, the link 46 is covered by the tension ring 44, as is illustrated in FIGS. 3A and 4A.

In the embodiments shown, the link 46 is provided on only one side of the jaws 34, 36. However, it is generally possible to provide a link on both sides of the jaws 34, 36. Furthermore, it is generally possible to provide more than one link on one side of the jaws 34, 36 or on both sides of the jaws 34, 36.

The link 46 shown in FIGS. 3B and 4B has a curved shape and, in particular, an S-like shape providing the link 46 with spring-like properties. Thereby the link 46 also exerts a restoring force on the jaws 34, 36, when the jaws 34, 36 are spread apart by the needle 24, as shown in FIG. 1. The link 46 thus aids the tension ring 44 in biasing the jaws 34, 36 towards each other.

It is to be appreciated that the link 46 does not necessarily need to have an S-like shape, but it may also have a Z-like shape or any other shape which is suitable to provide the link 46 with spring-like properties.

The base portion 30, the jaws 34, 36 and the link 46 are integrally formed from a plastic material, for example, by injection moulding. Alternatively, the base portion 30, the jaws 34, 36 and the link 46 may be made from a metal material.

As can be seen from FIGS. 3B and 4B, the jaws 34, 36 are slightly angled towards each other in the region of the tension ring 44, resulting in the outer profile of the needle safety device 28 being tapered towards the head portions 38, 40.

In order to hold the tension ring 44 in a fixed position on the jaws 34, 36, two part annular protrusions 48 are formed on the outer surface of the jaws 34, 36, as shown in FIGS. 1, 2 and 3. The part annular protrusions 48 are spaced apart a distance matched to the axial dimension of the tension ring 44. The part annular protrusions 48 can thus receive the tension ring 44 between themselves, thereby functioning as guides for the tension ring 44 and securing the position of the tension ring 44 on the jaws 34, 36. In addition to or instead of the part annular protrusions 48, a depression or groove 49 may be formed in the outer surface of the jaws 34, 36, as shown in FIG. 3C.

It is to be noted that the part annular protrusions 48 and depression or groove 49 are optional, i.e. the needle safety device 28 can also be made without any part annular protrusions, depression or groove, as shown in FIGS. 4A and 4B.

As can be seen from FIGS. 3 and 4, a locking shoulder 50 is formed at the side of each head portion 38, 40 facing the tension ring 44. The locking shoulder 50 and the tension ring 44 together form a recess or groove 52.

Referring again to FIG. 1, an annular locking protrusion 54 is formed on the inner surface of the main body 12 of the wing housing 10 and protrudes into the chamber 22.

Prior to use of the intravenous catheter apparatus, i.e. when the needle safety device 28 is inserted into the chamber 22 and the needle 24 extends all the way through the needle safety device 28 and the wing housing 10, the annular locking protrusion 54 is received in the recess 52 defined by the tension ring 44 and the head portion 38 of the first jaw 34, which is forced away from the second jaw 36 due to the angled end section 42 supported on the needle 24.

Because of the annular locking protrusion 54 engaging into the recess 52 of the needle safety device 28 in the spread apart state of the jaws 34, 36, the needle safety device 28 is secured against movement relative to the main body 12 in the axial direction. Specifically, the needle safety device 28 cannot be pulled out of the wing housing 10, since the locking shoulder 50 of the head portion 38 of the first jaw 34 engages behind the annular locking protrusion 54.

As is illustrated in FIG. 5, the annular locking protrusion 54 is a distance away from the proximal end 16 of the main body 12, this distance being in the range of 5 mm to 6 mm or more.

The annular locking protrusion 54 may have a substantially rectangular profile with rounded edges (FIG. 6A), a rounded profile similar to a Gaussian curve or a semi-sinusoidal curve (FIG. 6B), or any other profile suitable for locking of the needle safety device 28 in the wing housing 10.

Preferably, the locking protrusion 54 is of continuous annular shape. However, it is generally also possible to consider an annular locking protrusion 54 having one or more interruptions.

When the needle 24 is being withdrawn from a patient and, thus, from the intravenous catheter apparatus, the needle 24 is simultaneously pulled through the needle safety device 28. As has been mentioned above, as long as the jaws 34, 36 are in their spread apart position, the needle safety device 28 is secured against axial movement relative to the main body 12, i.e. the needle safety device 28 remains in the wing housing 10.

However, as soon as the tip 56 of the needle 24 moves into the needle safety device 28, i.e. passes beyond the angled end section 42 of the first jaw 34, the first jaw 34 snaps back or collapses into its relaxed position, as shown in FIG. 3, due to the restoring force exerted by the tension ring 44 and the link 46.

When the first jaw 34 adopts its relaxed position, the locking protrusion 54 is released from the recess 52 and the locking shoulder 50 of the first head portion 38 is disengaged from the locking protrusion 54. As a result, the safety device 28 is free to move relative to the main body 12 in the axial direction. Specifically, the needle safety device 28 can now be pulled out of the wing housing 10, as is indicated in FIG. 2.

As is illustrated in FIGS. 3A and 7, the position of the enlargement 26 formed on the outer surface of the needle 24 is selected such that the enlargement 26 abuts the base portion 30 of the needle safety device 28 as soon as the needle tip 56 has passed the free end of the second jaw 36.

Since the maximum outer dimension of the needle 24 in the region of the enlargement 26 is larger than the dimension of the bore in the base portion 30, which is adapted to the principal outer profile or circumference of the needle 24, the needle 24 can not be further pulled out of the needle safety device 28 than is shown in FIG. 3. In other words, because of the enlargement 26, the needle safety device 28 cannot slide off the needle 24 during normal use of the needle 24 and needle safety device 28, i.e. unless an excessive external force is applied to the needle 24 and/or the needle safety device 28.

With the needle tip 56 captured inside the needle safety device 28, the needle tip 56 is covered by the angled end section 42 of the first jaw 34. At the same time, the tension ring 44 prevents the needle tip 56 from coming sideways out of the needle safety device 28. Hence, the needle tip 56 is safely guarded by the needle safety device 28.

Figure 8:
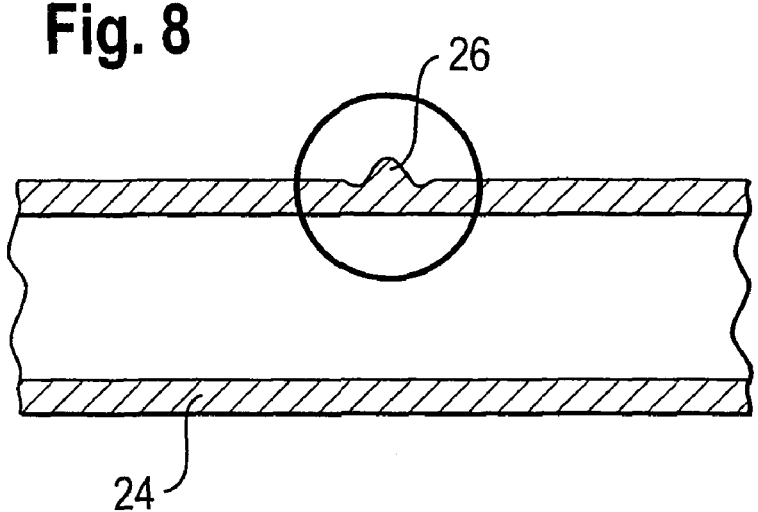
FIG. 8 shows a cross-sectional view of the needle of FIG. 7 in the region of the enlargement which has been formed by welding.
Figure 9:
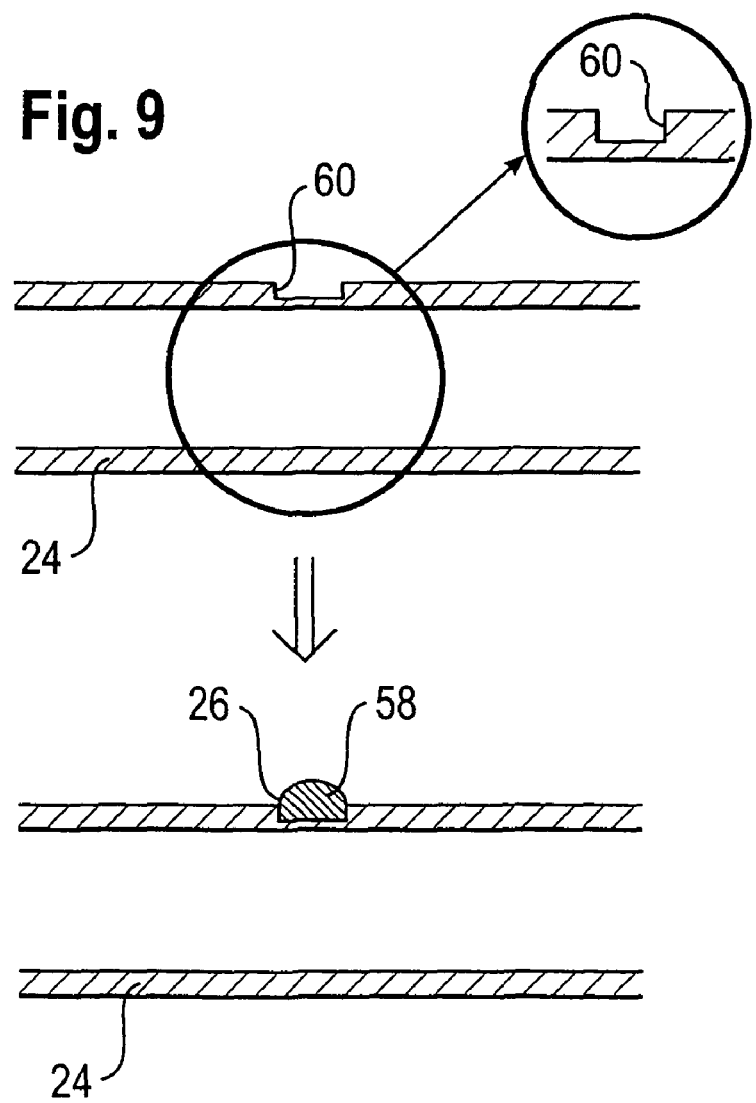
FIG. 9 shows cross-sectional views of the needle of FIG. 7 in the region of the enlargement, illustrating the formation of the enlargement by a deposition process.

Referring to FIGS. 8 and 9, the enlargement 26 of the needle 24 is formed such that the inner profile of the needle 24 is not affected by the formation of the enlargement 26, i.e. remains substantially unchanged. Thereby, when the needle 24 penetrates a vein, the flow of blood through the needle 24 will not be adversely affected by the enlargement 26.

The enlargement 26 may be formed as a bump by subjecting the needle 24 to concentrated heat at a localized area, for example, using a welding process, such as a build-up welding process or a laser welding process, with or without addition of additional material (FIG. 8).

Alternatively, the enlargement 26 may be formed by dispensing additional material 58 onto the outer surface of the needle 24, such as an adhesive, a resin or a metal material. The additional material 58 may be placed in a recess 60 which has been formed in the outer surface of the needle 24 prior to dispensing the additional material 58. However, formation of the recess 60 is optional.

Although only one enlargement 26 is shown in FIGS. 7 to 9, it is to be noted that more than one enlargement may be present on the outer surface of the needle 24.

REFERENCE NUMERAL LIST 10 wing housing
12 main body
14 distal end
16 proximal end
17 catheter
18 port
20 wing
22 chamber
24 needle
26 enlargement
28 needle safety device
30 base portion
34 first jaw
36 second jaw
38 head portion
40 head portion
42 angled end section
44 tension ring
46 link
48 annular protrusion
49 groove
50 locking shoulder
52 recess
54 locking protrusion
56 needle tip
58 additional material
60 recess

The invention claimed is:

1. A needle safety device for a medical device, the needle safety device comprising:
   a base portion having a bore extending in an axial direction therethrough for receiving a needle and
   two opposing jaws extending from the base portion generally in the axial direction and each having a head portion in the region of its free end, wherein at least one of the head portions forms a locking shoulder for securing the needle safety device in a housing of the medical device; and
   an elastic element surrounding the jaws in a region between the base portion and the locking shoulder, wherein the elastic element and the jaws are configured such that the jaws can be spread apart against a restoring force of the elastic element in order to allow the needle received in the bore to extend all the way through the needle safety device, and the elastic element having an axial length such that the elastic element covers a substantial portion of a space between the jaws to prevent the needle tip from protruding sideways out of the needle safety device.

2. The needle safety device of claim 1, wherein the axial length of the elastic element ranges from about one fifth of the length of the jaws to about three quarters of the length of the jaws.

3. The needle safety device of claim 1, wherein the elastic element is made from a material having elastic properties or an elastic material.

4. The needle safety device of claim 1, wherein the elastic element comprises a tension ring completely surrounding the jaws, or a clamp or bracket.

5. The needle safety device of claim 1, wherein the jaws are connected to each other by at least one link in a region between the base portion and the head portions.

6. The needle safety device of claim 5, wherein the link is arranged in the region of the elastic element.

7. The needle safety device of claim 5, wherein the link is provided on only one side of the jaws.

8. The needle safety device of claim 5, wherein first and second links are provided on opposite sides of the jaws.

9. The needle safety device of claim 5, wherein the at least one link is formed to have spring-like properties such that the jaws can be spread apart against a restoring force of the link.

10. The needle safety device of claim 5, wherein the at least one link has a curved shape.

11. The needle safety device of claim 1, wherein the base portion, the jaws, and a link connecting the jaws, are integrally formed.

12. The needle safety device of claim 1, wherein the base portion, the jaws and a link connecting the jaws each comprise a different material or combination of materials.

13. The needle safety device of claim 1, wherein at least one of the jaws has an angled end section at its free end, which extends towards the other one of the jaws in a direction generally perpendicular to the axial direction.

14. The needle safety device of claim 13, wherein the length of the angled end section is selected such that the angled end section is supported on the needle when the needle extends all the way through the needle safety device, thereby spreading the jaws apart far enough for the shoulder of the head portion of the jaw having the angled end section to engage with the housing of the medical device for securing the needle safety device in the housing.

15. A needle for a medical device, the needle comprising an inner profile, a principal outer profile and a needle tip, the needle further comprising an enlargement in the region of the needle tip, wherein the enlargement is formed from an increase of the outer profile of the needle in at least one direction, whereas the inner profile remains substantially unchanged.

16. The needle of claim 15, wherein the enlargement is formed by subjecting the needle to concentrated heat at a localized area using, for example, a welding process such as a laser welding process, with or without addition of additional material.

17. The needle of claim 15, wherein the enlargement is formed from additional material dispensed onto the outer surface of the needle.

18. The needle in accordance with of claim 17, wherein the additional material is selected from at least one of a plastic material, an adhesive, a resin and a metal material.

19. An intravenous catheter apparatus comprising:
a needle having an inner profile, a principal outer profile and a needle tip, the needle further comprising an enlargement in the region of the needle tip, wherein the enlargement is formed from an increase of the outer profile of the needle in at least one direction so that the inner profile remains substantially unchanged;
a needle safety device slidably arranged on the needle for protecting the needle tip, the needle safety device comprising:
a base portion having a bore extending in an axial direction therethrough for receiving the needle, the bore being adapted to the principal outer profile of the needle;
two opposing jaws extending from the base portion generally in the axial direction and each having a head portion in the region of its free end, wherein at least one of the head portions forms a locking shoulder for securing the needle safety device in a housing of the medical device; and
an elastic element surrounding the jaws in a region between the base portion and the locking shoulder, wherein the elastic element and the jaws are configured such that the jaws can be spread apart against a restoring force of the elastic element in order to allow the needle received in the bore to extend all the way through the needle safety device, and wherein the elastic element has an axial length such that the elastic element covers a substantial portion of a space between the jaws to prevent the needle tip from protruding sideways out of the needle safety device.

20. The intravenous catheter apparatus of claim 19, wherein a locking protrusion for engaging with the needle safety device is formed on an inner surface of a catheter hub of the intravenous catheter apparatus.

21. The intravenous catheter apparatus of claim 20, wherein the locking protrusion has a substantially rectangular profile with rounded edges or a rounded profile similar to a Gaussian curve or a semi-sinusoidal curve.

22. The intravenous catheter apparatus of claim 19, wherein the enlargement is formed by subjecting the needle to concentrated heat at a localized area.

23. The intravenous catheter apparatus of claim 19, wherein the enlargement is formed from additional material dispensed onto the outer surface of the needle.

24. The intravenous catheter apparatus of claim 23, wherein the additional material is selected from at least one of a plastic material, an adhesive, a resin and a metal material.

25. The needle safety device of claim 2, wherein the axial length of the elastic element is in the range of about one-third of the length of the jaws.

26. The needle safety device of claim 10, wherein the at least one link has an S-like or Z-like shape.

27. The needle safety device of claim 5, wherein the at least one link has a substantially straight shape.

* * * * *